United States Patent [19]
Yabusaki et al.

[11] Patent Number: 5,137,822
[45] Date of Patent: Aug. 11, 1992

[54] TRANSFORMED YEASTS HAVING STEROID-HYDROXYLASE ACTIVITY AND PROCESS FOR HYDROXYLATION OF STEROIDS USING THE SAID TRANSFORMED YEASTS

[75] Inventors: Yoshiyasu Yabusaki, Hyogo; Toshiyuki Sakaki; Megumi Shibata, both of Osaka; Hideo Ohkawa, Hyogo, all of Japan

[73] Assignee: Director-General of Agency of Industrial Science & Technology an organ of The Ministry of Industrial Trade and Industry of Japan, Tokyo, Japan

[21] Appl. No.: 232,843

[22] Filed: Aug. 16, 1988

[30] Foreign Application Priority Data

Aug. 19, 1987 [JP] Japan .................... 62-204101

[51] Int. Cl.$^5$ ............... C12N 9/10; C12N 15/63; C12N 1/18; C12N 15/81
[52] U.S. Cl. .................. 435/193; 435/320.1; 435/256; 435/172.3; 435/942; 935/28; 935/37; 935/69
[58] Field of Search .......... 435/155, 255, 256, 32, 435/69.1, 320.1, 172.3, 256, 193; 935/28, 60, 69

[56] References Cited

U.S. PATENT DOCUMENTS 4,766,068 8/1988 Oeda .................... 435/69.1

FOREIGN PATENT DOCUMENTS 0060057 9/1982 European Pat. Off. .

OTHER PUBLICATIONS

K. Yanagibashi et al. (1986) J. Biol. Chem. 261:8429–8433.
Sakaki et al., "Expression of Bovine Cytochrome P450c21 and Its Fused Enzymes with Yeast NADPH-Cytochrome P450 Reductase in *Saccharomyces cerevisiae*", DNA and Cell Biology, 1990, vol. 9 No. 8, pp. 603–614.
Sakaki et al., "Expression of Bovine Cytochrome P450c17 cDNA in *Sacharomyces cerevisiae*", DNA, 1989, vol. 8, No. 6, pp. 409–418.
Ammerer, Methods in Enzymol. 101, 192 (1983), "Expressions of Genes in Yeast Using the ADCl Promoter".
Zuber et al., J. Biol. Chem., 261, 2475 (1986), "Bovine Adrenocortical Cytochrome P-450$_{17\alpha}$".
Zuber et al., Science, 234, 1258 (1986) "Expression of Bovine 17-Hydroxylase Cytochrome P-450 cDNA in Nonsteroidogenic (COS1) Cells".
Oeda et al., DNA, 4, 203 (1985) "Expression of Rat Liver Cytochrome P-45OMC cDNA in *Saccharomyces cerevisiae*".
Sakai et al., J. Biochem., 99, 741 (1986) "Monooxygenase Activity of Saccharomyces cerevisiae Cells Transformed with Expression Plasmids Carrying Rat Cytochrome P-450MC cDNA".

Primary Examiner—Richard A. Schwartz
Assistant Examiner—Johnny F. Railey, II
Attorney, Agent, or Firm—Cushman, Darby & Cushman

[57] ABSTRACT

Transformed yeasts with yeast expression plasmid containing yeast alcohol dehydrogenase promoter and bovine adrenocortical cytochrome P-450$_{17\alpha}$ cDNA, which produce bovine adrenocortical cytochrome P-450$_{17\alpha}$, and processes for producing 17-hydroxypregnenolone and 17-hydroxyprogesterone which comprises 17-hydroxylating pregnenolone or progesterone to 17-hydroxypregnenolone or 17-hydroxyprogesterone, respectively, with the said transformed yeasts.

10 Claims, 8 Drawing Sheets

FIG. 4A

```
                                GAATTCCCAGCTCTTTGTCCTGACTGCTGCCACCCAGACACA
                                        10         20         30         40         50         60
ATGTGGCTGCTCCTGGCTGTCTTCTGCTCACCCTGCTCCTGCCTATTTATTTTGGCCCAAGACC
 M  W  L  L  L  A  V  F  L  L  T  L  A  Y  L  F  W  P  K  T
        70         80         90        100        110        120
AAGCACTCTGGTGCCAAGTACCCCAGGAGCCTCCCATCCCCTGCCCCTGGTGGGCAGCCTG
 K  H  S  G  A  K  Y  P  R  S  L  P  S  L  P  L  V  G  S  L
       130        140        150        160        170        180
CCGTTCCTCCCCAGACGTGGCCAGCAGCAAGAACTTCTTCAAGCTGCAGGAAAAATAT
 P  F  L  P  R  R  G  Q  Q  H  K  N  F  F  K  L  Q  E  K  Y
       190        200        210        220        230        240
GGCCCCATCTATTCCTTTCGTTTGGGTTCCAAGACGACTGTGATGATTGGACACCACCAG
 G  P  I  Y  S  F  R  L  G  S  K  T  T  V  M  I  G  H  H  Q
       250        260        270        280        290        300
TTGGCCAGGAGGTGCTTCTCAAGAAGGGCAAGGAATTCTCTGGGCGTCCCAAAGTGGCC
 L  A  R  E  V  L  L  K  K  G  K  E  F  S  G  R  P  K  V  A
       310        320        330        340        350        360
ACTCTAGACATCCTGTCAGACAACCAAAAGGGCATTGCCTTTGCCGACCATGGTGCCCAC
 T  L  D  I  L  S  D  N  Q  K  G  I  A  F  A  D  H  G  A  H
       370        380        390        400        410        420
TGGCAGCTGCATCGGAAGCTGGCACTGAATGCCTTTGCCCTGTTCAAGGATGGCAACCTG
 W  Q  L  H  R  K  L  A  L  N  A  F  A  L  F  K  D  G  N  L
```

FIG. 4A (CON'T)

```
           430         440         450         460         470         480
     AAGTTAGAGAAGATCATTAATCAGGAAGCCAATGTGTCTCTGTGATTCCTGGCCACCCAG
      K  L  E  K  I  I  N  Q  E  A  N  V  L  C  D  F  L  A  T  Q 490         500         510         520         530         540
     CATGGAGAGGCCATAGATCTGTCCGAGCCTCTCTCTGGCGGTGACCAACATAATCAGC
      H  G  E  A  I  D  L  S  E  P  L  S  L  A  V  T  N  I  I  S 550         560         570         580         590         600
     TTTATCTGCTTCAACTTCTCCTTCAAGAATGAGGATCCTGCCCTGAAGGCCATACAAAAT
      F  I  C  F  N  F  S  F  K  N  E  D  P  A  L  K  A  I  Q  N 610         620         630         640         650         660
     GTCAATGATGGCATCCTGGAGGTTCTGAGCAAGGAAGTTCTGTTAGACATATTCCCTGTG
      V  N  D  G  I  L  E  V  L  S  K  E  V  L  L  D  I  F  P  V 670         680         690         700         710         720
     CTGAAGATTTTCCCCAGCAAAGCCATGGAAAAGATGAAGGGTTGTGTTCAAACGCGAAAT
      L  K  I  F  P  S  K  A  M  E  K  M  K  G  C  V  Q  T  R  N 730         740         750         760         770         780
     GAATTGCTGAATGAAATCCTTGAAAAATGTCAGGAGAACTTCAGCAGTGATTCCATCACT
      E  L  L  N  E  I  L  E  K  C  Q  E  N  F  S  S  D  S  I  T 790         800         810         820         830         840
     AACTTGCTGCACATACTGATCCAAGCCAAGGTGAATGCAGAACAATAACAATGCTGGCCA
      N  L  H  I  L  I  Q  A  K  V  N  A  D  N  N  N  A  G  P
```

FIG. 4B

```
              850              860              870              880              890              900
GACCCAGGATTCAAAGCTGCTTCAAATAGACACATGCTCGCTACTATAGGGACATCTTC
 D  Q  D  S  K  L  L  S  N  R  H  M  L  A  T  I  G  D  I  F 910              920              930              940              950              960
GGGGCTGGTGTGGAGACCACCAGTCTCTGTGATAAAGTGGATCGTGGCCTACCTGCTACAC
 G  A  G  V  E  T  T  S  V  I  K  W  I  V  A  Y  L  L  H 970              980              990             1000             1010             1020
CATCCTTCGTTGAAGAAGAGGATCCAGGATGACATTGACCAGATTATAGGTTTCAATCGC
 H  P  S  L  K  K  R  I  Q  D  D  I  D  Q  I  I  G  F  N  R 1030             1040             1050             1060             1070             1080
ACCCCAACCATCAGTGACCGGAACCGCCTTGTCCTGCTGGAGGCCACCATCAGAGAAGTG
 T  P  T  I  S  D  R  N  R  L  V  L  L  E  A  T  I  R  E  V 1090             1100             1110             1120             1130             1140
CTCCGAATCCGGCCTGTGGCCCCTACGCTGATCCCCCACAAGGCTGTCATTGACTCCAGC
 L  R  I  R  P  V  A  P  T  L  I  P  H  K  A  V  I  D  S  S 1150             1160             1170             1180             1190             1200
ATTGGGACCTTACCATTGACAAAGGCACAGACGTTGTGTGTCAACCTGTGGCACTGCAT
 I  G  D  L  T  I  D  K  G  T  D  V  V  V  N  L  W  A  L  H 1210             1220             1230             1240             1250             1260
CACAGTGAGAAGGAGTGGCAGCATCCCGACCTGTTCATGCCCGAGCGCTTCTTGACCCCC
 H  S  E  K  E  W  Q  H  P  D  L  F  M  P  E  R  F  L  D  P
```

FIG. 4B (CON'T)

```
      1270       1280       1290       1300       1310       1320
ACGGGGACGGCAACTCATCATCTCGCCATCATTAAGCTACTTGCCCTTGAGCAGGACCCCGC
 T  G  T  Q  L  I  S  P  S  L  S  Y  L  P  F  G  A  G  P  R 1330       1340       1350       1360       1370       1380
TCCTGCGTAGGTGAGATGCTAGCCCGCCAGGAGCTCTTCCTCTTCATGTCCCGGCTGCTG
 S  C  V  G  E  M  L  A  R  Q  E  L  F  L  F  M  S  R  L  L 1390       1400       1410       1420       1430       1440
CAGAGGTTCAACCTGGAGATCCCGGATGATGGGAAGCTACCTTCTCTGGAGGGCCATGCC
 Q  R  F  N  L  E  I  P  D  D  G  K  L  P  S  L  E  G  H  A 1450       1460       1470       1480       1490       1500
AGTCTCGTCTTGCAGATCAAACCTTTCAAGGTGAAGATCGAGGTGCGCCAGGCCTGGAAG
 S  L  V  L  Q  I  K  P  F  K  V  K  I  E  V  R  Q  A  W  K 1510       1520       1530
GAAGCCCAGGCTGAGGGTAGCACCCCATGACTCCACCCTATGTGACCCCACCGCACAGA
 E  A  Q  A  E  G  S  T  P  *

ATTAGAGGAGCTCCCCACCCTCTCCACCATTCCTTCCTCCCGCCACTCTGCCT

TCTTTCCCAGCCTGCAGCCCTGGCAGTGATGTGCATTAAACAGTTTCTTTCTCAAAACA

AAAAAGGAATTC
```

TRANSFORMED YEASTS HAVING STEROID-HYDROXYLASE ACTIVITY AND PROCESS FOR HYDROXYLATION OF STEROIDS USING THE SAID TRANSFORMED YEASTS

FIELD OF THE INVENTION

The present invention relates to yeast expression plasmids containing bovine adrenocortical cytochrome P-450$_{17\alpha}$cDNA inserted between the yeast ADH promoter and terminator, to transformed yeasts harboring the said expression plasmids and to processes for producing 17-hydroxyprogesterone and 17-hydroxypregnenolone using the said transformed yeasts.

BACKGROUND OF THE INVENTION

Cytochrome P-450 (hereinafter referred to as "P-450") is a hemoprotein existing in various kinds of living organisms widely from microorganisms to mammals. It has been known that, in order for P-450 to be functional, it is essential to contain a heme in its molecule.

In mammalian adrenals, several types of P-450 species exist, regulating the biosynthesis of steroid hormones. P-450$_{17\alpha}$is a member of the P-450 family found in microsomes in the adrenal cortex of mammals, and has 17-hydroxylase activity towards pregnenolone and progesterone, as well as C17-20-lyase activity towards 17hydroxypregnenolone and 17-hydroxyprogesterone.

Zuber et al. have elucidated the complete DNA sequence of the cDNA encoding the bovine adrenocortical cytochrome P-450$_{17\alpha}$(hereinafter referred to as P-450$_{17\alpha}$) [J. Biol, Chem. 261, 2475 (1986)]and introduced the cDNA in COS1 cells which originally have no ability to produce P-450$_{17\alpha}$and succeeded in expression of the cDNA in the COS1 cells [Science, 234, 1258 (1986)]. The COS1 cells hydroxylated pregnenolone and progesterone to 17-hydroxypregnenolone and 17-hydroxyprogesterone, and subsequently converted them to dehydroepiandrosterone and androstenedione, respectively.

It has been known that, when using progesterone as a substrate, for example P-450$_{17\alpha}$exhibits the 17$\alpha$-hydroxylase activity to form 17-hydroxyprogesterone, and the C$_{17-20}$-lyase activity to subsequently convert 17-hydroxyprogesterone into androstenedione. The P-450$_{17\alpha}$produced from the said COS1 cells exhibits both of the 17$\alpha$ hydroxylase activity and C$_{17-20}$-lyase activity. The C$_{17-20}$-lyase activity of the P-450$_{17\alpha}$is about 5% of the 17$\alpha$-hydroxylase activity of the P-450$_{17\alpha}$.

For the production of cortisol through the following production route using P-450$_{17\alpha}$as a hydroxylating agent, the C$_{17-20}$-lyase activity of the P-450$_{17\alpha}$is considered undesirable because it causes side reactions and by-products:

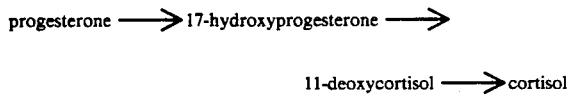

progesterone ⟶ 17-hydroxyprogesterone ⟶

11-deoxycortisol ⟶ cortisol

Accordingly, as a hydroxylating agent, the P-450$_{17\alpha}$with no or least C$_{17-20}$-lyase activity as against the 17-hydroxylase activity is desirable, because the production of by-products can be avoided. From this viewpoint, the said COS1 cells have a defect as a steroid hydroxylating agent.

The present inventors have previously succeeded in the expression of rat cytochrome P-450MC cDNA in Saccharomyces cerevisiae at high expression levels using yeast alcohol dehydrogenase gene promoter (ADH promoter). However, the same cDNA could not be expressed at all when it was connected to GAL10 promoter. The present inventors have also constructed yeast expression plasmids by inserting the DNA sequence coding for bovine adrenal cytochrome P-450scc, which has a side-chain cleaving activity against cholesterol, in an expression plasmid containing the ADH promoter and transformed Saccharomyces cerevisiae with the resulting plasmids, but the transformant yeasts only produced inactive P-450scc with no heme in its molecule. Thus, it was found that it was very difficult to forecast whether or not a particular mammalian P-450 species was able to successfully be expressed in given circumstances, and that each mammalian P-450 species differed from others in terms of its expressible conditions.

The present inventors have studied on the hydroxylation of steroids with P-450$_{17\alpha}$and, as a result of the study, have found that the yeasts which are transformed with the plasmids constructed by inserting the cDNA coding for the bovine adrenocortical cytochrome P-450$_{17\alpha}$in a yeast expression plasmid having ADH promoter produce active P-450$_{17\alpha}$containing a heme in its molecule, and that the P-450$_{17\alpha}$produced by said yeasts is very active in 17-hydroxylase activity, but almost inactive in C$_{17-20}$-lyase activity. The yeasts producing the P-450$_{17\alpha}$quantitatively converted progesterone to 17-hydroxyprogesterone but did not cleave the carbon side chain at 17-20 positions. It has now become possible to selectively hydroxylate steroids with the P-450$_{17\alpha}$-producing-yeasts of the present invention.

The yeasts of the present invention have various advantages over the animal cells of Zuber et al. as a hydroxylating agent for steroids in that, for example, they can easily be grown at a higher cell density (the highest cell density; yeasts: $10^9$ cells/ml; animal cells: $10^6$ cells/ml) and in a shorter period of time (doubling time; yeasts: 2-3 hours; animal cells: ca. 70 hours) and therefore the hydroxylation of steroids can be performed within a shorter period of time with a smaller vessel with the transformed yeasts of the invention.

SUMMARY OF THE INVENTION

The present invention provides yeast expression plasmids containing the ADH promoter and bovine adrenocortical cytochrome P-450$_{17\alpha}$cDNA, transformed yeasts with the said expression plasmids, which produce the P-450$_{17\alpha}$in the cells and a process for producing the P-450$_{17\alpha}$which comprises culturing the said transformed yeasts in a suitable medium.

It also provides a process for producing 17-hydroxyprognenolone and 17-hydroxyprogesterone, which comprises 17-hydroxylating pregnenolone or progesterone, respectively, with the said transformed yeasts or the P-450$_{17\alpha}$produced by the said transformed yeasts.

The chemical structure of the pregnenolone, progesterone, 17-hydroxypregnenolone and 17-hydroxyprogesterone are shown below:

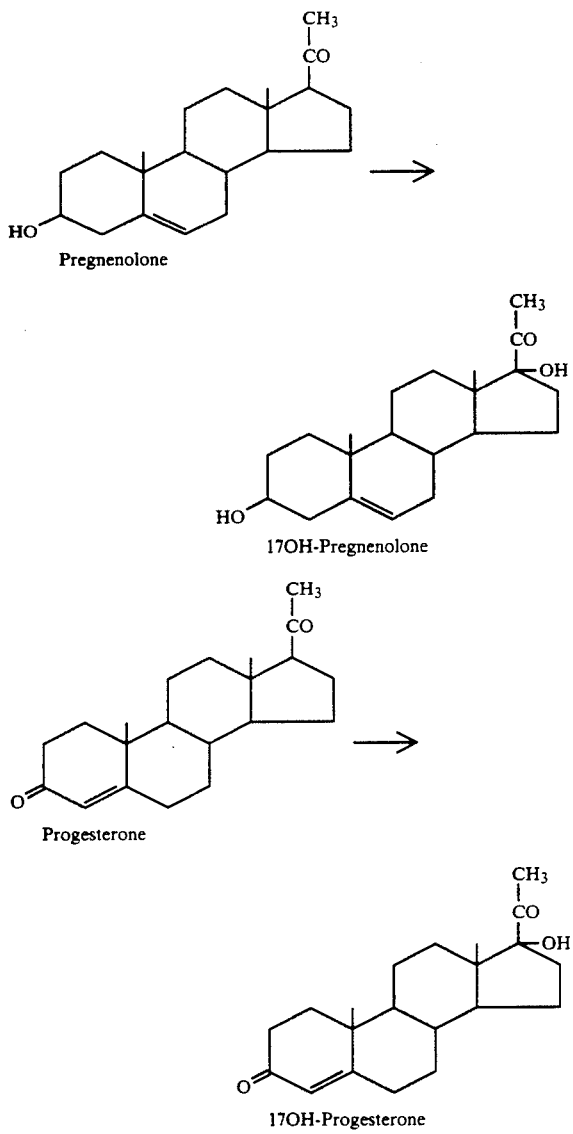

Pregnenolone

17OH-Pregnenolone

Progesterone

17OH-Progesterone

BRIEF DESCRIPTION OF THE DRAWINGS

FIG. 4(a) and (b) shows the DNA sequence of the P-450$_{17\alpha}$cDNA inserted in the plasmids pAα1 and pAα2 and the deduced amino acid sequences thereof.

Aα1 and AAH indicate S. cerevisiae AH22(pAα1) and AH22(pAAH5), respectively.

Figure 6:
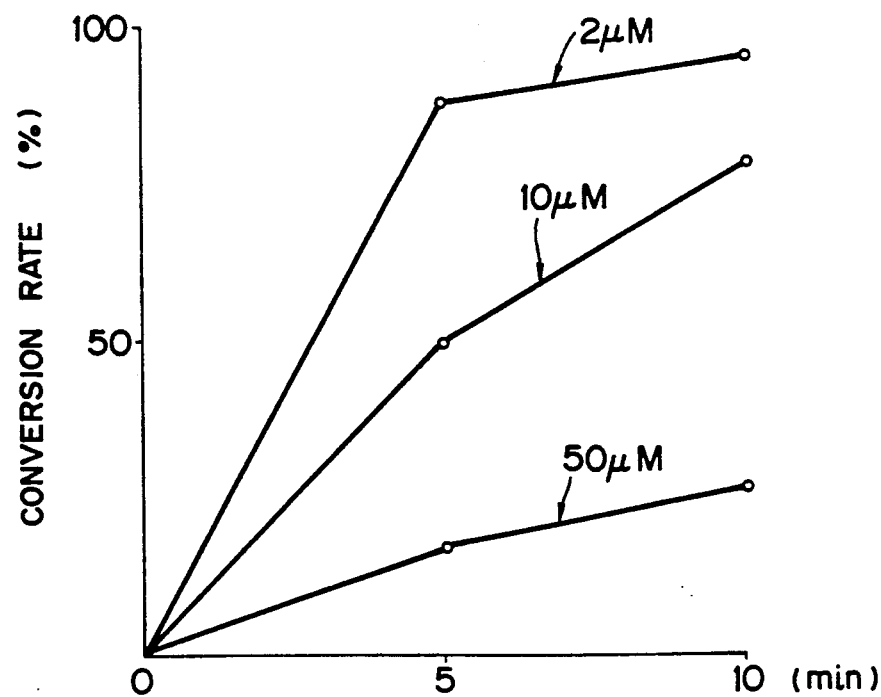

FIG. 6 shows the 17-hydroxylase activity of the microsomal fraction prepared from S. cerevisiae AH22-(pAα1) on progesterone. The values 2μM, 10μM and 50μM, above the curves indicate the concentrations of the substrate. Values at the vertical line indicate the conversion rates of progesterone to 17-hydroxyprogesterone, and those at the horizontal line indicate the period of the incubation.

DETAILED DESCRIPTION OF PREFERRED EMBODIMENTS

A more detailed description of the present invention will be given hereinbelow:

The plasmid of the present invention can be constructed by inserting a DNA sequence coding for the bovine adrenocortical cytochrome P-450$_{17\alpha}$into an expression vector plasmid containing ADH promoter and terminator, preferably yeast expression vector pAAH5 (this plasmid can be prepared by the method disclosed in "Methods in Ezymology", 101 part C, p. 192-201) according to the conventional procedures.

The DNA encoding the bovine adrenocortical cytochrome P-450$_{17\alpha}$used in the present invention has been reported as mentioned above, and can be prepared readily by the method disclosed in the said publication.

The transformation of yeasts with the expression plasmid of the present invention can be performed by known methods, such as the alkaline metal method or the protoplast method. As the host yeasts, Saccharomyces cerevisiae, in particular, S. cerevisiae AH22 is preferably used, but the host yeast to be used in the invention is not particularly limited.

The process for producing 17-hydroxyprogesterone and 17-hydroxypregnenolone can be conducted by incubating progesterone or pregnenolone, respectively, with the yeast of the invention in a suitable medium.

In conducting the process, the cultivation of the yeasts can be carried out in the conventional ways. In this process, the conversion rates of the reactants are as high as more than 95%.

The produced 17-hydroxyprogesterone does not remain in the cells but is secreted from the yeast cells. Therefore, it can readily be recovered from the culture medium after the cells are removed by, for example, centrifugation or filtration. The removed cells can be used again for the process.

In the same manner, 17-hydroxypregnenolone can be isolated from the medium. In this case, the yeast cells take-up about 50% of the produced 17-hydroxypregnenolone and therefore the recovery rate is lower than pAα1; <u>AAGCTT</u>GAATTCCAGCTCTTTGTCCTGACTGCTGCCACCCAGACACA<u>ATG</u> ...
     Hind III                                                                       Met pAα2; <u>AAGCTT</u>AAAAAAA<u>ATG</u> ...
     Hind III       Met that of the case of the production of 17-hydroxyprogesterone.

The P-450$_{17\alpha}$-producing yeasts of the present invention have great advantages in that they selectively convert progesterone into 17-hydroxyprogesterone with showing almost no C$_{17\text{-}20}$-lyase activity against 17-hydroxyprogesterone.

17-Hydroxypregnenolone and 17-hydroxyprogesterone produced by the process of the present invention can be converted to cortisol by any of the known methods.

The present invention will be more precisely illustrated by the following examples. The present invention is not limited only to the disclosed example, but it includes the improvements or modifications usually carried out in the field of the present invention.

EXAMPLE 1

Preparation of cDNA encoding bovine adrenocortical cytochrome P-450$_{17\alpha}$ Total RNA was prepared from bovine adrenal by the guanidinium thiocyanate method, and the poly(A)RNA was isolated using an oligo(dT)-cellulose column. The poly(A)RNA was treated at 65° C. for 5 minutes, and then size-fractioned by sucrose density gradient (10–30%) centrifugation (270,000 x g, 1 h). The RNA fraction a little larger than 18sS rRNA marker was subjected to cDNA synthesis with the Amersham cDNA synthesis system.

In addition, cDNA library was prepared with cDNA cloning system using λgt11.

Based on the information on the sequence of the cDNA encoding the bovine adrenocortical P-450$_{17\alpha}$, the following three 30-mers were synthesized:

5' GCT CAG AAC CTC CAG GAT GCC ATC ATT GAC 3'
5' CAC AGG GAA TAT GTC TAA CAG AAC TTC CTT 3'
5' TTC CAT GGC TTT GCT GGG GAA AAT CTT CAG 3'

With these DNA $^{32}$P-labelled by the kinasing method, about 25,000 plaques of the said cDNA library were subjected to the plaque hybridization. The hybridization and washing were conducted at 50° C. Phage DNA was isolated from the positive clone and digested with restriction enzyme EcoRI to give 1.4 kb and 0.32 kb fragments. After these fragments were inserted into EcoRI site of the commercially available cloning vector pUC18 and the DNA sequences of the fragments were determined by the dideoxy sequencing method to confirm that the cDNA codes for the bovine adrenocortical P-450$_{17\alpha}$.

EXAMPLE 2

Figure 1:
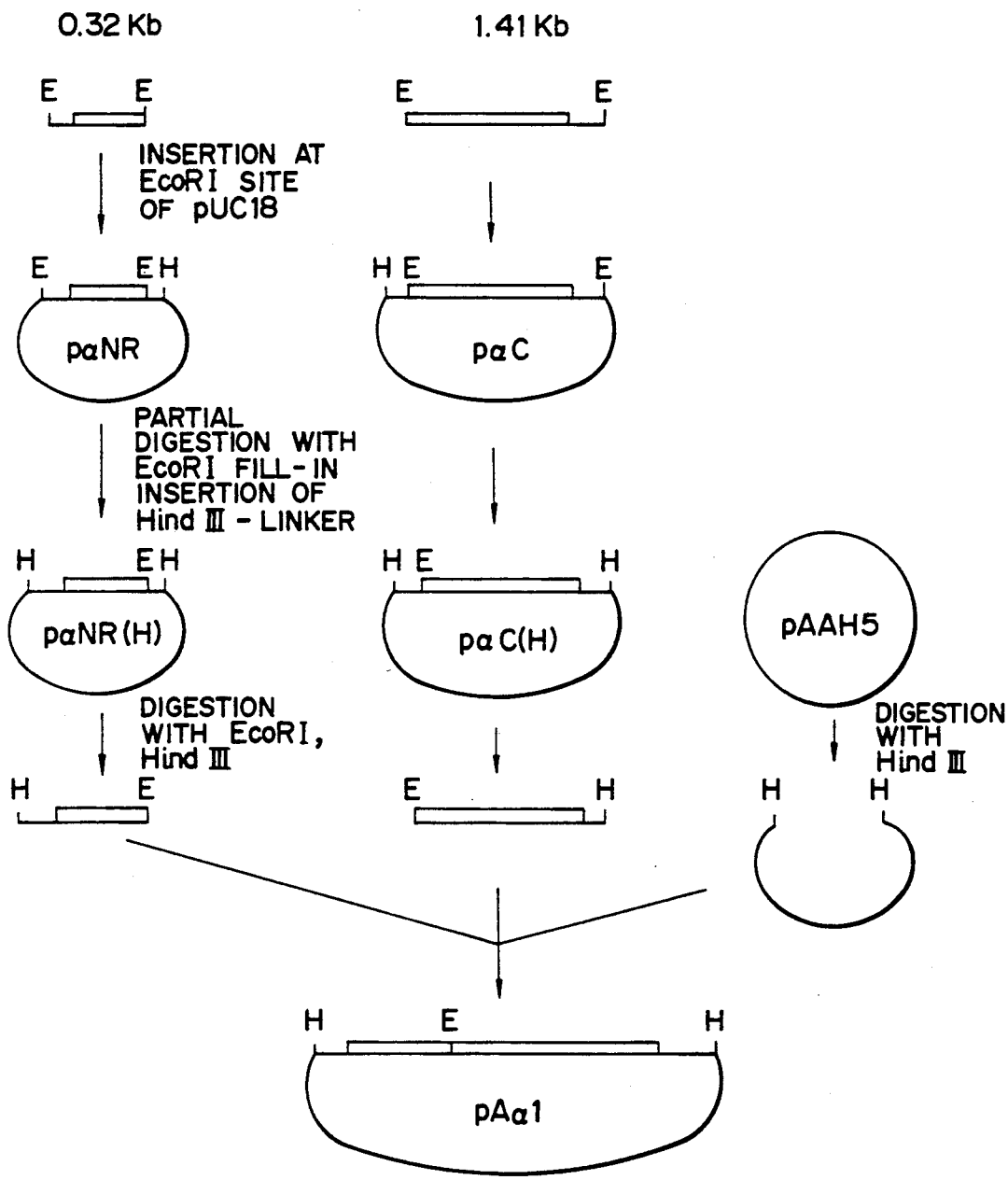
FIG. 1 is a diagram showing the construction of the expression plasmid pAα1.

Construction of expression plasmid pAα1

λgt11-phage containing the cDNA coding for the P-450$_{17\alpha}$was digested with EcoRI and subjected to electrophoresis on low melting point agarose gel to give DNA fragments of 0.32 kb and 1.41 kb. These fragments were mixed and ligated with a commercially available cloning vector pUC18 which had been previously digested with EcoRI, followed by the treatment with alkaline phosphatase. E. coli JM109 strain was transformed with the resulting DNA, and the plasmid DNA was isolated from the transformants to give plasmid pαNR and PαC as shown in FIG. 1. These plasmids were partially digested with EcoRI and filled-in, and synthetic Hind III linker was ligated to them. The reaction mixtures were used to transform E. coli DH1. Plasmid DNA was isolated from the resulting transformants to give plasmids pαNR(H) and pαC(H) as shown in FIG. 1. By digestion of these plasmids with EcoRI and Hind III, DNA fragments of 0.33 kb and 1.42 kb were isolated. These fragments were ligated with yeast expression vector pAAH5 (available from Washington Research Foundation, and producible by the method disclosed in "Methods in Enzymology", 101 part C, p. 192–201) which had previously been digested with Hind III and treated with alkaline phosphatase. E. coli DH1 was transformed with the reaction mixture. Plasmid DNA was isolated from the transformants and digested with EcoRI and BamHI to confirm that the DNA is of the structure of FIG. 1, and named pAα1.

EXAMPLE 3

Figure 2:
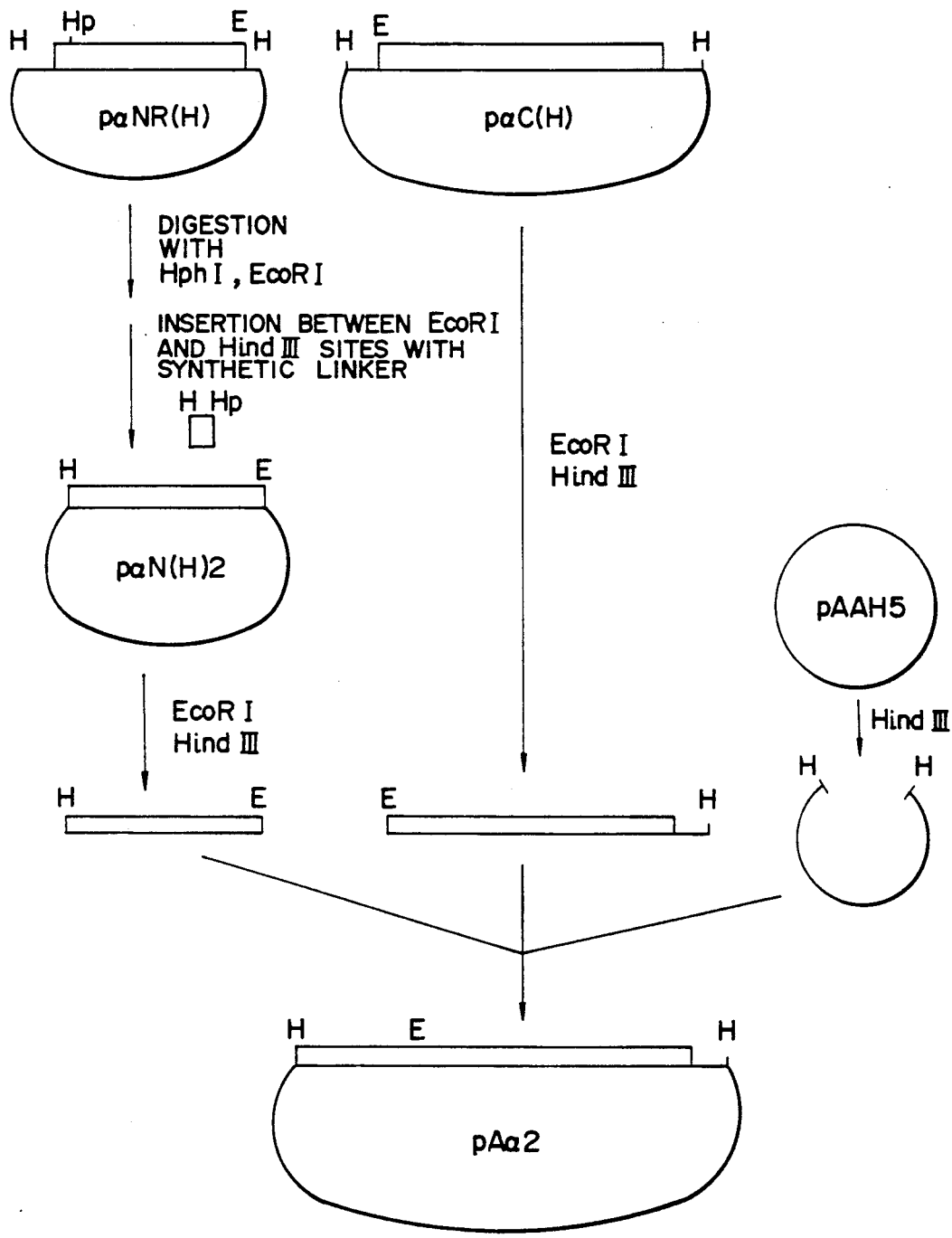
FIG. 2 is a diagram showing the construction of the expression plasmid pAα2. In these FIGS. 1 and 2, E indicates EcoRI site and H indicates Hind III site. The open square indicates the coding region of the P-450$_{17\alpha}$.
Figure 3:
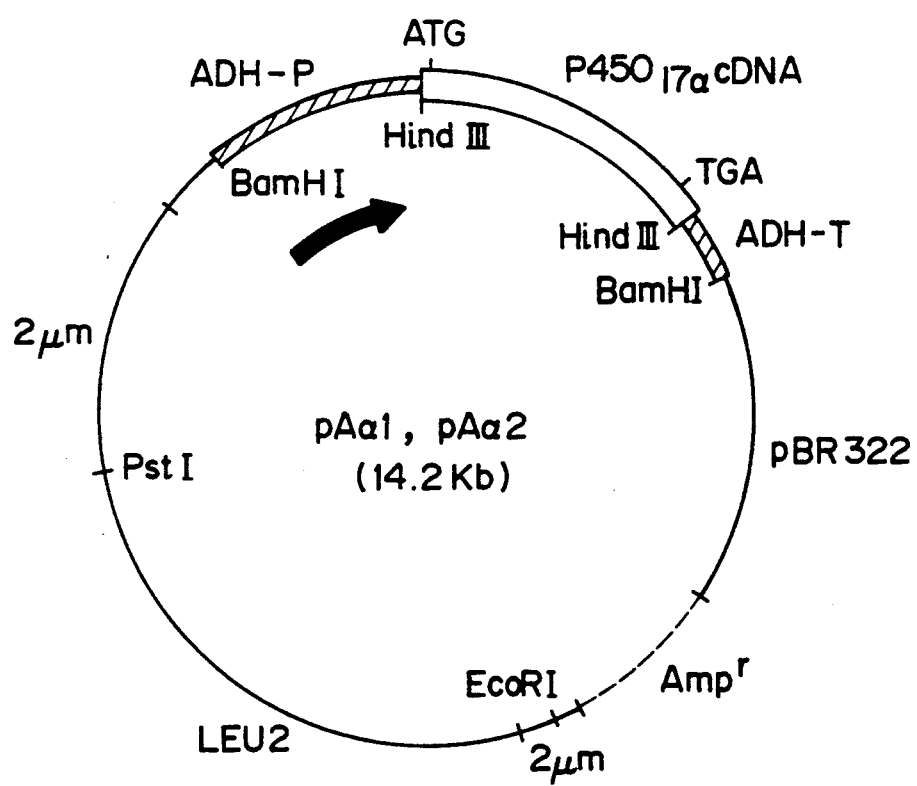
FIG. 3 shows the structures of the expression plasmids pAα1 and pAα2. The plasmids pAα1 and pAα2 are different from each other in the sequence of the linkage region between the ADH promoter and the initiation codon of the cDNA encoding the P-450$_{17\alpha}$. The DNA sequence of the linkage region is shown below.

Construction of expression plasmid pA2α (FIG. 2)

The plasmid pαNR(H) prepared in Example 2 was digested with EcoRI and HphI and about 250 bp fragment which codes for the amino-terminal region of the P-450$_{17\alpha}$was isolated. This DNA and the synthetic linker of the following sequence were inserted into Hind III-EcoRI site of plasmid pUC19 to give plasmid pαN(H)2:

5'- AGCTTAAAAAAATGTGGCTGCTCCTGGCTGTC-3'
3'- ATTTTTTTACACCGACGAGGACCGACA-5'

(so designated as to have Hind III site and HphI site at the ends)

About 290 bp DNA fragment was isolated from pαN(H)2 by digesting pαN(H)2 with Hind III and EcoRI.

The plasmid pαC(H) obtained in Example 2 was digested with Hind III and EcoRI to give about 1.4 kb DNA fragment which codes for the carboxyl-terminal region of the P-450$_{17\alpha}$. The EcoRI-Hind III fragments isolated from the pαN(H)2 and pαC(H)2 were combined with the yeast expression vector pAAH5 which had previously been digested with Hind III and treated with alkaline phosphatase, and the mixture was ligated. E. coli DH1 was transformed with the reaction mixture. Plasmid DNA was isolated from the transformants, and the DNA structure was analyzed by digestion with EcoRI and BamHI. The resulting expression plasmid was named pAα2.

EXAMPLE 4

Transformation of yeasts with plasmid pAα1 and pAα2

Saccharomyces cerevisiae AH22 was cultivated in 1.0 ml of YPD medium (1% yeast extract, 2% polypeptone and 2% glucose) at 30° C. for 18 hours, while the medium was being shaken, and the cells were harvested using centrifugation. The cells were suspended in 1.0 ml of a 0.2M LiCl solution and centrifuged to give pellets. To the pellets were added 20 μl of a 1M LiCl solution, 30 μl of a 70% polyethylene glycol 4000 solution and about 1.0 μg of pAα1 or pAα2 in a 10 μl volume. After the mixture was well mixed, it was incubated at 30° C. for 1 hour. Then, 140 μl of distilled water was added to the mixture and stirred. The resulting mixture was spread onto an SD-synthetic medium plate (2.0% glucose, 0.67% yeast nitrogen base without amino acids, 20 μg/ml histidine and 2% agar) and incubated at 30° C. for 3 days to give transformated Saccharomyces cerevisiae AH22(pAα1), or AH22(pAα2) containing plasmid pAα1 or pAα2, respectively.

EXAMPLE 5

Determination of the amount of P-450$_{17α}$ containing heme

From 200 ml each of the culture media (SD-synthetic culture medium, cell density: $1.5 \times 10^7$ cells/ml) of *Saccharomyces cerevisiae* AH22(pAα1) and AH22(pAα2), the cells were harvested and resuspended in 10 ml each of 100 mM potassium phosphate buffer (pH 7.0), which was then centrifuged to give pellets. The pellets were suspended in 2.0 ml of 100 mM potassium phosphate buffer (pH 7.0), and 1.0 ml each of the suspension was poured into two cuvettes. Carbon monoxide was bubbled into the sample cuvettes and 5–10 mg each of dithionite was added to the cuvettes. After the mixture was stirred, the difference spectrum of 400–500 nm was measured, and the concentrations of P-450$_{17α}$ was calculated from the values. The results showed that both the *S. cerevisiae* AH22(pAα1) and AH22(pAα2) produced about $1 \times 10^5$ molecules/cell of P-450$_{17α}$.

EXAMPLE 6

Preparation of microsomal fraction of the yeasts

The yeasts of the present invention produce P-450$_{17α}$, and almost all of the produced P-450$_{17α}$ exists in the microsomes of the yeasts. Therefore, the microsomal fraction of the yeasts can be used in the monooxigenation process. The followings are an example of the procedure for the preparation of the microsomal fraction: After *S. cerevisiae* AH22(pAα1) was grown to a cell density of $2.0 \times 10^7$ cells/ml, the cells were harvested from 1.8 l of the culture broth and suspended in 50 ml of a buffer A (10 mM Tris-HCl (pH 7.5), 2M sorbitol, 0.1 mM DTT and 0.2 mM EDTA). After 20 mg of Zymolyase 100,000 was added to the suspension, the mixture was incubated at 30° C. for 1 hour. The resulting spheroplasts were harvested by centrifugation (5,000 x g for 10 minutes). They were suspended in 100 ml of buffer A and centrifuged. By repeating the centrifugation, the spheroplasts were washed. They were resuspended in 30 ml of a buffer solution (10 mM Tris-HCl (pH 7.5), 0.65M sorbitol and 0.1 mM DTT) and subjected to ultra sonication at 50W for 5 minutes. The mixture was centrifuged at 10,000 x g for 20 minutes, and the supernatant was again centrifuged at 125,000 x g for 70 minutes. The precipitates were suspended in 2.0 ml of 0.1M potassium phosphate buffer (pH 7.4).

EXAMPLE 7

Figure 5:
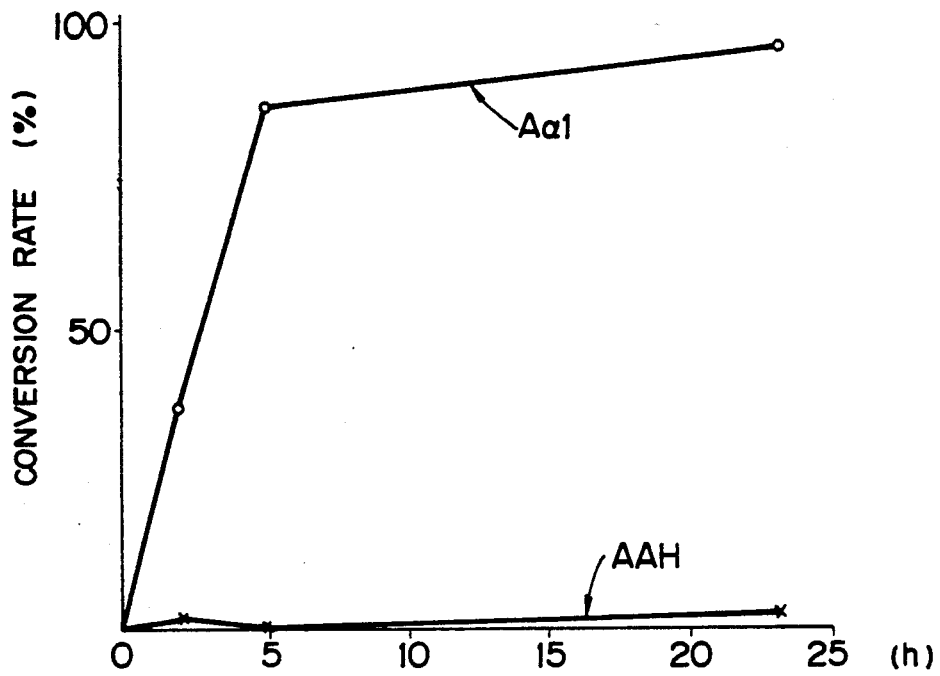
FIG. 5 shows the 17-hydroxylase activity of the S. cerevisiae AH22(pAα1) against progesterone. Values at the vertical line indicate the conversion rates of progesterone to 17-hydroxyprogesterone, and those at the horizontal line indicate the period of the cultivation.

Determination of 17-hydroxylase activity of *S. cerevisiae* AH22(pAα1) against progesterone and pregnenolone:

*S. cerevisiae* AH22(pAα1) and AH22(pAAH5) were separately grown to each $7 \times 10^6$ cells/ml in an SD-synthetic-medium (2.0% glucose, 0.67% yeast nitrogen base without amino acids, and 20 μg/ml histidine). To 5.0 ml each of the medium was added 50 μl of 1 mM progesterone in ethanol solution containing 10 μCi of [$^3$H]-progesterone (or 50 μl of 1 mM pregnenolone in ethanol solution containing 10 μCi of [3H]-pregnenolone) and the mixture was cultured while shaking. Each 1.0 ml of the medium was sampled at 0, 2, 5 and 23 hours and centrifugated. After 2.0 ml of dichloromethane was added to 0.8 ml of the supernatant, the mixture was vigorously agitated and centrifugated. The dichloromethane layer (1.0 ml) was evaporated to dryness and the residue was dissolved in 20 μl of ethanol/ethyl acetate (1:1 by volume). Ten μl of the solution was applied to TLC. The TLC was developed with chloroform containing 25% ethyl acetate at room temperature for 50 minutes and radioautographed. The silica gel of the spot on the film was scraped out from the plate and the radio activity of the gel was measured with a liquid scintillation counter. It was found that, as shown in FIG. 5, *S. cerevisiae* AH22(pAα1) converted progesterone to 17-hydroxyprogesterone by 87% through 5 hour-incubation, and 97% through 23 hour-incubation. No activity was observed with control AH22(pAAH5). On the other hand, AH22(pAα1) converted pregnenolone to 17-hydroxypregnenolone by 28% through 2 hour-incubation, but AH22(pAAH5) showed no activity.

EXAMPLE 8

Determination of 17-hydroxylase activity of microsomes of AH22(pAα1) against progesterone A mixture of 3.6 ml of a 100 mM potassium phosphate buffer (pH 7.4) and 100 μl of a 20 mM NADPH aqueous solution was preincubated at 37° C. for 5 minutes. To the mixture, 200 μl of the microsomal fraction (containing 0.28 nmol of P-450$_{17α}$) derived from AH22(pAα1) and 80 μl each of 0.1 mM, 0.5 mM and 2.5 mM pregesterone in ethanol containing 3 μCi of [$^3$H]-progesterone (final concentration; 2 μM, 10 μM and 50 μM, respectively) were added, and the mixture was incubated at 37° C. with shaking. Each 1.0 ml of the mixture was sampled at 0, 2 and 10 minutes and centrifugated. After 2.0 ml each of dichloromethane was added, the sample mixtures were vigorously agitated and centrifugated. The dichloromethane layer (1.0 ml) was evaporated to dryness and the residue was treated in the same manner as in Example 6. As the result, it was found that, through 5 minutes-reaction, 88% of the added progesterone was converted to 17-hydroxyprogesterone when the concentration of progesterone was 2 μM, 49% when the concentration was 10 μM, and 17% when the concentration was 50 μM (see FIG. 6). The control AH22(pAAH5) showed no activity.

What we claim is:

1. A yeast expression plasmid which comprises yeast alcohol dehydrogenase promoter and bovine adrenocortical cytochrome P-450$_{17α}$cDNA, wherein the promoter is operably-linked to the cDNA.

2. An expression plasmid pAα1.

3. An expression plasmid pAα2.

4. Yeasts which are transformed with yeast expression plasmids which plasmids comprise yeast alcohol dehydrogenase promoter and bovine adrenocortical cytochrome P-450$_{17α}$cDNA, wherein the promoter is operably-linked to the cDNA, and which plasmids produce bovine adrenocortical cytochrome P-450$_{17α}$.

5. A yeast harboring an expression plasmid selected from plasmids pAα1 or pAα2.

6. A transformed yeast of claim 4 or 5 which belongs to *Saccharomyces cerevisiae*.

7. *Saccharomyces cerevisiae* AH22(pAα1).

8. *Saccharomyces cerevisiae* AH22(pAα2).

9. A process for producing bovine adrenocortical cytochrome P-450$_{17α}$, which comprises culturing yeasts which are transformed with yeast expression plasmids which plasmids comprise yeast alcohol dehydrogenase promoter and bovine adrenocortical cytochrome P-450$_{17α}$cDNA, wherein the promoter is operably-linked to the cDNA, and which plasmids are capable of producing produce bovine adrenocortical cytochrome P-450$_{17α}$ in a suitable medium.

10. A process for producing 17-hydroxypregnenolone and 17-hydroxyprogesterone by culturing the yeasts defined in claim 4.